United States Patent [19]

Kitaguchi

[11] Patent Number: 4,688,014
[45] Date of Patent: Aug. 18, 1987

[54] SEMICONDUCTOR TYPE GAS SENSOR HAVING TWO TERMINALS

[75] Inventor: Hisao Kitaguchi, Toyonaka, Japan
[73] Assignee: New Cosmos Electric Co., Ltd., Japan
[21] Appl. No.: 750,226
[22] Filed: Jun. 28, 1985

Related U.S. Application Data

[63] Continuation-in-part of Ser. No. 582,512, Feb. 22, 1984, abandoned.

[30] Foreign Application Priority Data

Apr. 11, 1983 [JP] Japan .................................. 58-62075

[51] Int. Cl.⁴ ............................................. H01L 7/00
[52] U.S. Cl. ..................................................... 338/34
[58] Field of Search ............. 338/34, 35; 73/23, 27 R; 422/94–98

[56] References Cited

U.S. PATENT DOCUMENTS

| | | | |
|---|---|---|---|
| 3,901,067 | 8/1975 | Boardman, Jr. et al. | 422/98 X |
| 4,234,542 | 11/1980 | Romine | 338/34 X |
| 4,338,281 | 7/1982 | Treitinger et al. | 338/34 X |
| 4,396,899 | 8/1983 | Ohno | 73/27 R X |

FOREIGN PATENT DOCUMENTS

| | | | |
|---|---|---|---|
| 55-166032 | 12/1980 | Japan | 422/98 |
| 56-008537 | 1/1981 | Japan | 73/27 R |
| 56-51655 | 5/1981 | Japan | 338/34 |
| 56-112638 | 9/1981 | Japan | 338/34 |

Primary Examiner—Harold Broome
Assistant Examiner—Marvin M. Lateef
Attorney, Agent, or Firm—Jones, Tullar & Cooper

[57] ABSTRACT

A gas senor having two terminals and comprising a heater having a positive temperature coefficient of resistance and a gas sensitive semiconductor covering the heater, connected to the heater at least at their opposite ends and having a negative temperature coefficient of resistance. The coefficients of the heater and the semiconductor are so selected as to offset each other in such a manner that a combined resistance of said heater and said semiconductor is maintained substantially constant at operation temperatures.

4 Claims, 10 Drawing Figures

SEMICONDUCTOR TYPE GAS SENSOR HAVING TWO TERMINALS

This is a continuation-in-part of co-pending application Ser. No. 582,512 filed on Feb. 22, 1984, now abandoned.

BACKGROUND OF THE INVENTION

The present invention relates to semiconductor type gas sensors having two terminals and comprising a heater and a gas sensitive semiconductor covering the heater.

Gas sensors heretofore known include those of the type having a four-terminal structure wherein a heater circuit in the form of a platinum film or the like formed by vapor deposition and a gas sensing semiconductor circuit made of $SnO_2$ or like metal oxide are electrically insulated from each other by an insulation plate, and each of the heater and the semiconductor has a pair of terminals at its opposite ends. Gas sensors of another type are also known which comprise such a heater circuit and gas sensing semiconductor circuit connected together each at one end and which have three terminals, i.e., one at the connection and two at the other ends of the circuits.

These two types of gas sensors have the following drawback. When such gas sensors are energized in clean air, current passes through the heater and the gas sensing semiconductor. The heater develops heat according to Joule's law, heating the semiconductor, while the semiconductor itself also evolves heat owing to the passage of current therethrough. Thus the semiconductor is maintained at a given high temperature to exhibit a definite standard resistance. However, the amount of heat developed by the heater and the amount of heat evolved by the current through the semiconductor itself are not independent but influence each other in a complicated fashion. If the amount of heat developed by the heater is altered, for example, by variations in the voltage of the heater power source, the temperature of the semiconductor varies. Since the electric resistance of the semiconductor also varies with its temperature, the standard resistance then differs considerably from the normal value, with the result that the intensity of the output signal emitted by the gas sensor differs from the usual level even at the same gas concentration. On the other hand, a variation in the ambient temperature or humidity to which the gas sensor is exposed of course alters the standard resistance of the semiconductor. This further varies the temperature of the heater to change the amount of Joule heat produced by the heater, consequently greatly changing the resistance of the semiconductor.

SUMMARY OF THE INVENTION

The present invention has been accomplished to overcome the foregoing drawback.

Accordingly an object of the present invention is to provide a gas sensor having two terminals and comprising a heater having an appropriate positive temperature coefficient of resistance and a gas sensitive semiconductor having an appropriate negative temperature coefficient of resistance, the heater being covered with the semiconductor.

More specifically an object of the present invention is to provide a two-terminal gas sensor of the type described wherein the materials of the heater and the semiconductor are so selected that the positive temperature coefficient of resistance of the heater and the negative temperature coefficient of resistance of the semiconductor covering the heater offset each other. (For convenience sake, the term "negative temperature coefficient of resistance" is used although the resistance of the semiconductor does not change in proportion to temperature.)

According to the present invention, the two temperature coefficients of resistance are regulated by finely adjusting the materials to be used for the heater and the semiconductor, and the sensor is used in a temperature range in which the two coefficients thus regulated offset each other almost completely. This temperature range is realized by controlling the range of power supply voltages to be applied to the heater.

In particular, the heater constituting the gas sensor is formed of an alloy comprising platinum (Pt) as a principal ingredient. The semiconductor is a sintered metal oxide comprising tin oxide ($SnO_2$) as a principal ingredient. The alloy further contains desirably about 2 to 13 weight percent of rhodium (Rh) incorporated therein whereas the sintered metal oxide further contains desirably about 0.01–0.10% by atomic ratio of antimony pentoxide ($Sb_2O_5$). The atomic ratio means in general that the percent is based on a number of atoms of an element included in a compound or in a mixture. Therefore, said atomic ratio in this case is based on numbers of tin atoms and antimony atoms.

An excessive rhodium content higher than 13 weight percent imparts to the alloy an extremely high hardness which makes it difficult to work upon the alloy. Such a high content of rhodium also brings about a bad stability in course of time with respect to physical properties such as electric resistance of the alloy. Contrary to this, a lower content less than 2 weight percent of rhodium reduces a hardness as well as a tensile strength of the alloy to such a degree that a mechanical strength of said alloy cannot meet a need indispensable to the heater. Thus, the excessively high or low content of rhodium in the alloy is undesirable in the invention.

On the other hand, an excessive antimony pentoxide content higher than 0.10% by atomic ratio makes undesirably the semiconductor less sensitive to a gas because a change in electric resistance of said semiconductor becomes very small when exposed to the gas. Contrary to this, a very low antimony pentoxide content lower than 0.01% by atomic ratio makes excessively high the temperature coefficient of resistance of the semiconductor. Such a high coefficient of the semiconductor could not be offset by the temperature coefficient of the alloy.

In general, an adjustment of the antimony pentoxide content in the semiconductor is more difficult than adjustment of the rhodium content in the alloy because of a complicated manufacturing process of the sintered metal oxide semiconductor. Consequently, a suitable content of antimony pentoxide is predetermined at first, and then an experimental study is effected to find out the most suitable content of rhodium in the alloy. It is recomendable to select several contents of rhodium between 2 and 13 percent. The contents may be for instance 2%, 4%, 6%, 8%, 10% and 13% so as to prepare six kinds of gas sensor samples. These samples are then tested within a predetermined temperature range in which they have to operate. This test will reveal a change in a combined resistance of the heater and the semiconductor. If one of the six samples proves to have a combined resistance which shows no or little change thereof within a range of operating temperatures, it is thus possible to determine that an alloy in the heater of the sample has a sought composition containing the suited amount of rhodium. A positive temperature coefficient of resistance of the heater is therefore regarded to be offset by a negative temperature coefficient of resistance of the semiconductor.

The inventor has effected a series of researches based on such a practical rule and obtained a useful result in a gas sensor having a semiconductor composed of tin oxide and 0.052 atomic ratio percent of antimony pentoxide, the percent being employed in a sense of exemplification.

Rhodium contents in an alloy heater which was to be combined with the semiconductor were set at five levels in this case as shown in Table 1.

TABLE 1

| Rhodium content (wt. %) | 2 | 3.2 | 6.5 | 10.0 | 13.0 |
|---|---|---|---|---|---|
| Temperature coefficient of resistance (*) | 3.10 | 2.70 | 1.92 | 1.40 | 1.25 |

Note:
(*) the coefficient A × $10^3$ in an equation (2) described hereinafter

These five samples of gas sensors have been tested as to their changes in a combined resistance R (defined by an equation (1) described hereinafter).

Among them, one sample comprising a heater composed of platinum and 10.0 atomic ratio percent of rhodium has given the following result shown in Table 2 in an operating temperature range of 298° to 510° C.

TABLE 2

| Power supply voltage (V) | 2.6 | 2.7 | 2.8 | 2.9 | 3.0 |
|---|---|---|---|---|---|
| Operating temperature of Sensor (°C.) | 298 | 345 | 395 | 450 | 510 |
| Resistance of heater (Ω) | 12.75 | 13.35 | 13.98 | 14.67 | 15.43 |
| Resistance of semiconductor (Ω) | 45.81 | 39.88 | 35.00 | 31.14 | 28.11 |
| Combined resistance (Ω) | 9.97 | 10.00 | 9.99 | 9.97 | 9.97 |

This result teaches that the semiconductor containing 0.052 atomic ratio percent of antimony pentoxide has an "apparent" temperature coefficient of resistance which is almost perfectly offset by the temperature coefficient, i.e. $A = 1.40 \times 10^{-3}$, of the heater containing 10 wt.% of rhodium.

Similar results were also obtained in other semiconductors which contain approximately 0.01 and 0.10 atomic ratio percent of antimony pentoxide, respectively. Rhodium contents of the alloys were of values near 2% and 13%, respectively, whereby temperature coefficients of these heaters and semiconductors offset each other.

The gas sensor of the present invention thus constructed is not only simple in construction and easy to fabricate because the sensor has two terminals (two lead wires) but also gives gas detection output signals with improved reliability because the sensor is featured by reduced variations in standard resistance at varying temperatures.

The above and other objects and advantages of the present invention will become apparent from the following description.

DESCRIPTION OF THE PREFERRED EMBODIMENTS

Before describing embodiments, the basic principle of the present invention will be described first.

Figure 2:
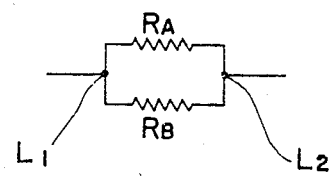
FIG. 2 is a diagram showing an equivalent circuit wherein a heater and a gas sensitive semiconductor are electrically connected together in parallel.

The gas sensor of the present invention differs from conventional three-terminal and four-terminal sensors of the semiconductor type in that a heater, viz., an electric resistor made of noble metal has the function of giving detection signals when it comes into contact with gas. When simplified as a model, the sensor comprises a heater having a resistance $R_A$ and a semiconductor haivng a resistance $R_B$ which are connected together in parallel as seen in FIG. 2. Accordingly the combined resistance R between the two terminals L1 and L2 of the sensor is given by the following equation.

$$R = \frac{R_A \cdot R_B}{R_A + R_B} \quad (1)$$

When gas is absorbed by the sensor, it is the resistance $R_B$ that varies. Consequently the combined resistance R also varies. However, when the temperature changes, the resistances $R_A$ and $R_B$ both vary.

Figure 1:
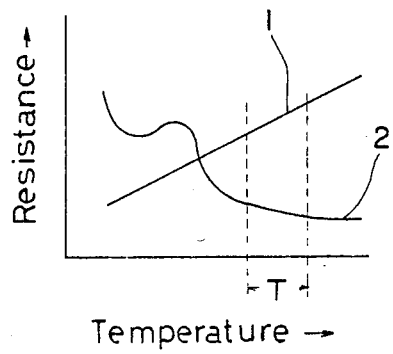
FIG. 1 is a diagram showing variations in the electric resistance, relative to temperature, of noble metal and a metal oxide for gas sensitive semiconductors.

The electric resistance $R_A$ of nobel metal generally varies with temperature as represented by a straight line 1 in FIG. 1. This relationship is expressed by the following equation.

$$R_A = R_{AO}(1+AT) \quad (2)$$

wherein $R_{AO}$ is the resistance at 0° C., A is a positive temperature coefficient of resistance, and T is temperature (°C.).

On the other hand, the electric resistance $R_B$ of the metal oxide forming the semiconductor varies with temperature as represented by a curve 2 in FIG. 1. In a stable temperature range T', the temperature dependence of the resistance $R_B$ is approximate to that of an intrinsic semiconductor. Accordingly the resistance $R_B$ is expressed by the following equation.

$$R_B = R_{BO} e^{-B/T''} \quad (3)$$

wherein $R_{BO}$ and B are positive coefficients, and $T''$ is absolute temperature (°K.).

Figure 3:
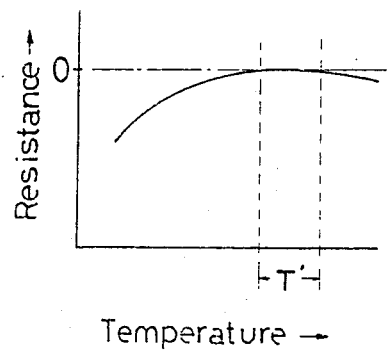
FIG. 3 is a diagram showing variations in the electric resistance of the equivalent circuit of FIG. 2 relative to temperature.

At temperatures lower than the stable range T', the resistance $R_A$ of noble metal is predominant, and the combined resistance R also exhibits a positive temperature coefficient of resistance (see FIG. 3), whereas at temperatures higher than the stable range T', the resistance $R_B$ of the semiconductor is predominant, so that the resistance R exhibits a negative temperature coefficient of resistance (see FIG. 3).

With the gas sensor of the present invention, optimum values are selected for the above parameters $R_{AO}$, A, $R_{BO}$ and B to provide the considerably wide stable range T' shown in FIG. 3. Insofar as the actual temperature of the sensor is included within this range, the combined resistance R apparently exhibits little or no temperature dependence. Accordingly even if the power supply voltage for the heater or the ambient temperature involves considerable variations, the standard resistance (represented by O in FIG. 3) of the sensor remains unchanged, permitting the sensor to afford gas detection signals with high reliability.

Figure 4:
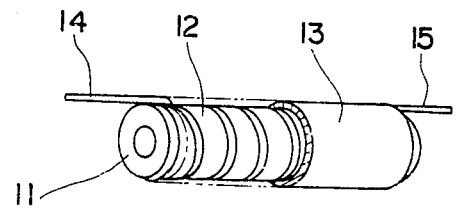
FIG. 4 is a perspective view partly broken away and showing an example of one embodiment of the invention.
Figure 5:
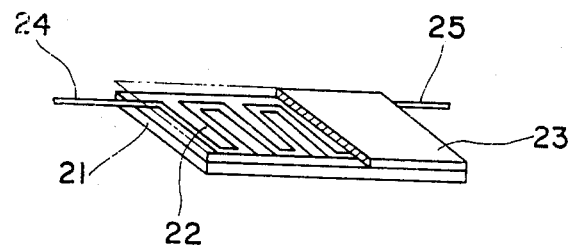
FIG. 5 and FIG. 6 are perspective views partly broken and showing other examples of the embodiment.
Figure 6:
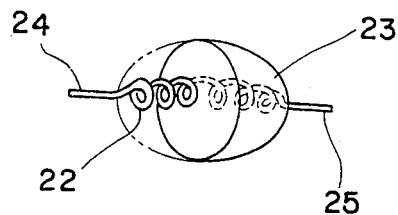

With reference to FIGS. 4 to 6, one embodiment will now be described in detail.

With this embodiment, a heater is in contact, over the entire length thereof, with a semiconductor.

FIG. 4 shows a gas sensor, an example of the embodiment, which comprises a hollow or solid cylindrical support member 11 having heat resistance and electrically insulating properties, and a heater 12 formed over the outer periphery of the support member 11 and made of vapor-deposited platinum film. The heater 12, which serves also as an electrode, is trimmed in a helical form so as to have a predetermined resistance. A gas sensitive semiconductor 13 of $SnO_2$ or like metal oxide covers the outer peripheral surface of the heater 12. Lead wires 14 and 15 are connected to opposite ends of each of the heater 12 and the semiconductor 13.

FIG. 5 shows another example of the same embodiment comprising a support member 21 in the form of a flat plate, a heater 22, a gas sensitive semiconductor 23 and lead wires 24, 25.

FIG. 6 shows still another example of the same embodiment. This sensor, which includes no support member, comprises a coiled heater 22 and a spheroidal gas sensitive semiconductor 23 covering the heater 22. Each component of the sensors of FIGS. 5 and 6 is the same as the corresponding component of the sensor of FIG. 4.

In the embodiment shown in FIGS. 4 to 6, the heaters 12, 22 are composed of 90 wt.% of platinum and 10 wt.% of rhodium, and the semiconductors 13,23 are composed of 99.948% of tin oxide and 0.052% of antimony pentoxide, based on the atomic ratio of number of tin atoms and antimony atoms.

Another embodiment of the invention comprises a heater and a semiconductor which are in contact with each other only at their opposite ends. With this structure, the heater and the semiconductor are much less likely to thermally affect each other than in the preceding embodiment. Consequently the standard resistance and output signals of the sensor are less susceptible to variations due to disturbances. Furthermore, sensors with the contemplated performance can be fabricated easily according to this embodiment.

Figure 7:
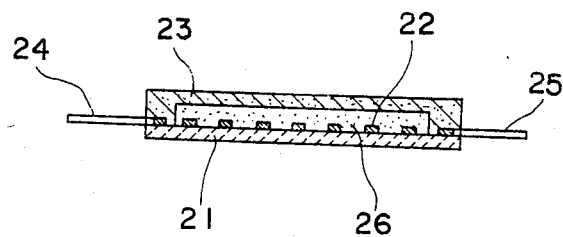
FIG. 7 is a sectional view showing another embodiment of the invention.

FIG. 7 shows an example of the embodiment which has the same appearance and shape as the one shown in FIG. 5. Throughout FIGS. 5 and 7, like parts are referred to by like reference numerals. The heater 22 and the gas sensitive semiconductor 23 are in contact with each other at their opposite ends and are electrically insulated from each other by an insulator 26 at their intermediate portions.

Each component of the sensor of FIG. 7 is made of the material as the corresponding component of the one shown in FIG. 4. The heater 22 and the semiconductor 23 in this embodiment have compositions similar to those in the aforementioned embodiment shown in FIGS. 4 to 6.

Figure 8:
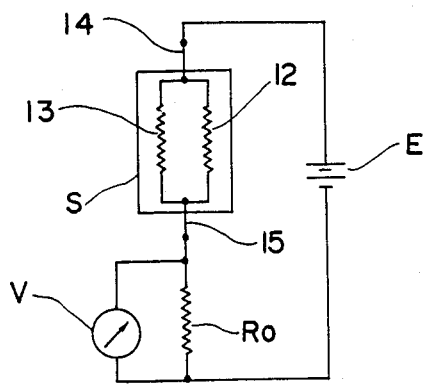
FIG. 8 and FIG. 9 are diagrams showing exemplary circuits including a semiconductor type gas sensor having two terminals and embodying the invention.
Figure 9:
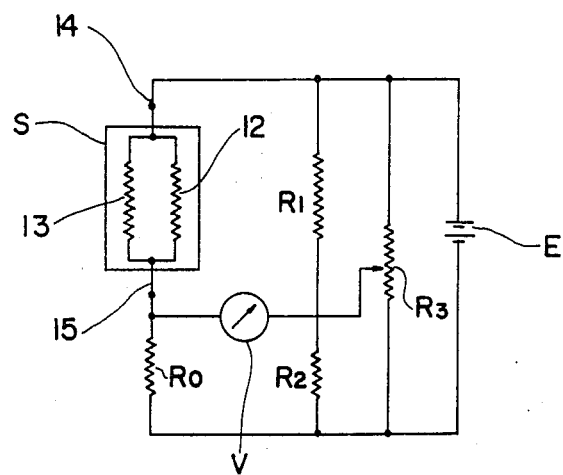

FIGS. 8 and 9 show exemplary circuits incorporating the two-terminal gas sensor of FIG. 4. The illustrated circuits include the gas sensor S, a power supply E (which also represents the power supply voltage), an output detector V (which also represents the output voltage), load resistors R0, R1, R2 and a zero adjusting variable resistor R3. The other parts are referred to each by the same corresponding numeral as in FIG. 4. The resistors R0, R1, R2 and R3 in FIG. 9 are of resistances 10Ω, 500Ω, 500Ω, and 10 kΩ, respectively. A power supply voltage is divided into halves by the resistor $R_3$ with its contacting member (shown as an arrow) set at a middle portion of said resistor $R_3$ when the performance test is effected as described hereinbefore referring to Table 2.

The same circuits as above can be fabricated with use of the two-terminal gas sensors of FIGS. 5 to 7.

Figure 10:
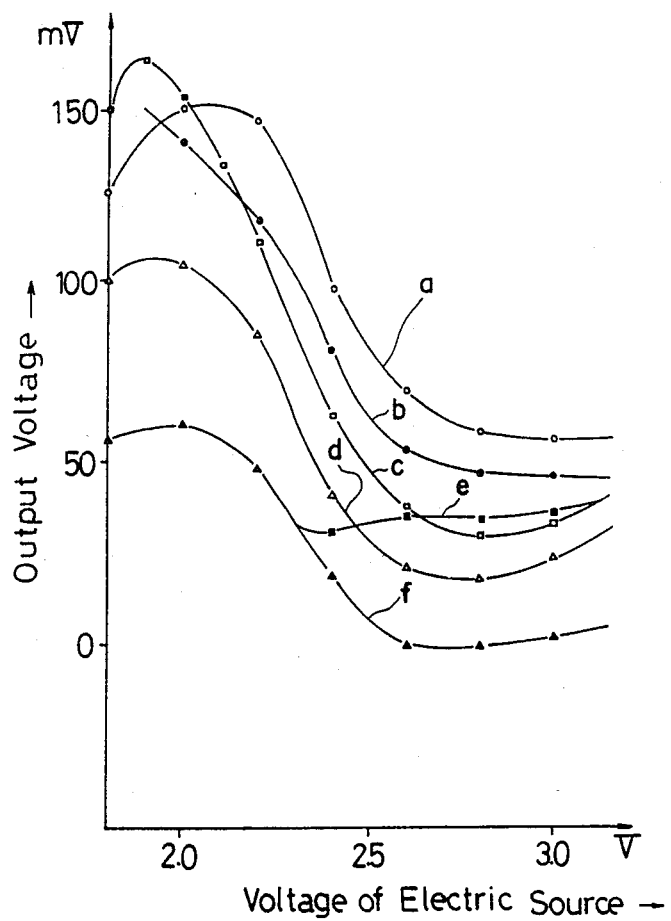
FIG. 10 is a diagram showing the relationship between the power supply voltage and the output voltage determined as exemplary experimental data according to the invention.

FIG. 10 shows exemplary data obtained according to the invention to illustrate the relationship between the power supply voltage E (corresponding to temperature) and the output voltage V. $H_2$ gas is represented by curve a, gas mixture of CO and $H_2$ (2:1) by curve b, $C_2H_5OH$ vapor by curve c, CO gas by curve d, $CH_4$ gas by curve e and base (air) by curve f. These gases were used at a concentration of 100 ppm. The average values achieved by ten two-terminal gas sensors were plotted to obtain each curve.

The diagram reveals that within the power supply voltage range of about 2.6 volts to about 3.0 volts, the output voltage remains almost unchanged despite variations in the power supply voltage.

I claim:

1. A gas sensor having two terminals and comprising:
   a heater having a positive temperature coefficient of resistance, and
   a gas sensitive semiconductor covering the heater at least at their opposite ends and having a negative temperature coefficient of resistance,
   the heater being an alloy composed of a principal ingredient and an auxiliary ingredient, the principal ingredient being platinum,
   the semiconductor being a sintered metal oxide composed of a principal ingredient and an auxiliary ingredient, the principal ingredient being tin oxide,
   wherein the kinds and contents of the auxiliary ingredients in the alloy and the sintered metal oxide are so selected that a combined resistance of said heater and said semiconductor are substantially constant corresponding to an offset of the temperature coefficient of resistance of the heater to the temperature coefficient of resistance of the semiconductor at operating temperatures, and wherein the auxiliary ingredient of the alloy is about 2 to 13 weight percent of rhodium and the auxiliary ingredient of the sintered metal oxide is about 0.01 to 0.10 atomic ratio percent of antimony pentoxide, the atomic ratio being based on the number of tin atoms and antimony atoms.

2. A gas sensor as defined in claim 1 wherein rhodium is contained in the alloy at about 10 weight percent, and antimony pentoxide is contained in the sintered tin oxide at about 0.052 atomic ratio percentage, and the operating temperature being included in a range of about 298° C. to about 510° C. corresponding to a power supply voltave range of about 2.6 volts to about 3.0 volts.

3. A gas sensor as defined in claim 2 wherein the heater and the semiconductor are in contact with each other over the entire lengths thereof.

4. A gas sensor as defined in claim 2 wherein the heater and the semiconductor are in contact with each other only at their opposite ends.

* * * * *